US 7,913,540 B2

(12) United States Patent
Brasfield

(10) Patent No.: US 7,913,540 B2
(45) Date of Patent: Mar. 29, 2011

(54) ODOR SCREENING SYSTEM

(76) Inventor: Freddie R. Brasfield, Knoxville, TN (US)

(*) Notice: Subject to any disclaimer, the term of this patent is extended or adjusted under 35 U.S.C. 154(b) by 342 days.

(21) Appl. No.: 11/859,851

(22) Filed: Sep. 24, 2007

(65) Prior Publication Data

US 2009/0077908 A1    Mar. 26, 2009

(51) Int. Cl.
*G01N 33/497* (2006.01)
(52) U.S. Cl. ...................................................... 73/23.34
(58) Field of Classification Search ................. 73/23.34, 73/23.2, 23.42, 864.33
See application file for complete search history.

(56) References Cited

U.S. PATENT DOCUMENTS

| | | | | |
|---|---|---|---|---|
| 3,357,257 A | * | 12/1967 | Herndon et al. ............ | 73/863.33 |
| 3,883,739 A | * | 5/1975 | Jenkins ........................ | 250/304 |
| 4,022,054 A | | 5/1977 | Biederman | |
| 4,202,200 A | * | 5/1980 | Ellson .......................... | 73/31.05 |
| 4,411,156 A | * | 10/1983 | Lowe ............................ | 73/866 |
| 4,896,547 A | * | 1/1990 | Arney et al. ................. | 73/863.81 |
| 4,987,767 A | * | 1/1991 | Corrigan et al. ............. | 73/23.36 |
| 5,109,691 A | * | 5/1992 | Corrigan et al. ............. | 73/23.36 |
| 5,753,832 A | * | 5/1998 | Bromberg et al. .......... | 73/864.81 |
| 5,915,268 A | * | 6/1999 | Linker et al. ................. | 73/23.2 |
| 6,018,984 A | * | 2/2000 | McGinley et al. ........... | 73/23.34 |
| 6,073,499 A | * | 6/2000 | Settles ......................... | 73/864.81 |
| 6,295,860 B1 | * | 10/2001 | Sakairi et al. ................ | 73/23.41 |
| 6,334,365 B1 | * | 1/2002 | Linker et al. ................ | 73/864.81 |
| 6,366,203 B1 | * | 4/2002 | Burns ........................... | 340/551 |
| 6,375,697 B2 | * | 4/2002 | Davies ........................... | 55/340 |
| 6,558,626 B1 | * | 5/2003 | Aker et al. ..................... | 422/91 |
| 6,610,977 B2 | * | 8/2003 | Megerle ......................... | 250/287 |
| 6,708,572 B2 | * | 3/2004 | Jenkins et al. .............. | 73/864.33 |
| 6,782,845 B1 | * | 8/2004 | Schmidt et al. ............... | 119/419 |
| 6,790,249 B2 | * | 9/2004 | Davies ........................... | 55/340 |
| 6,823,714 B2 | * | 11/2004 | Megerle ......................... | 73/23.2 |
| 6,919,202 B2 | * | 7/2005 | Lewis et al. .................. | 435/287.1 |
| 7,023,339 B2 | * | 4/2006 | Stomski ......................... | 340/540 |
| 7,091,856 B2 | | 8/2006 | Tibi et al. | |
| 7,141,786 B2 | * | 11/2006 | McGann et al. ............. | 250/287 |
| 7,180,441 B2 | * | 2/2007 | Rowe et al. .................... | 342/22 |
| 7,357,043 B2 | * | 4/2008 | Cumming et al. .......... | 73/864.33 |
| 2003/0085348 A1 | * | 5/2003 | Megerle ......................... | 250/287 |
| 2004/0232054 A1 | * | 11/2004 | Brown et al. ................. | 209/552 |
| 2006/0150872 A1 | | 7/2006 | Mesinger | |
| 2007/0056392 A1 | * | 3/2007 | Cumming et al. .......... | 73/864.33 |

FOREIGN PATENT DOCUMENTS

WO    WO 2004085251 A1 * 10/2004

* cited by examiner

*Primary Examiner* — John Fitzgerald
(74) *Attorney, Agent, or Firm* — Luedeka Neely & Graham PC

(57) ABSTRACT

An apparatus and method are provided for screening odor emitters for one or more target odors. A screening station is adapted to permit an odor emitter, such as a pedestrian or vehicle, to pass through the screening station. An observation room contains a dog trained to identify at least one target odor. An airflow inducer; directs airflow through the screening station. A porous passage allows airflow from the screening station to the observation room. Air flows through the screening station to entrain odors emitted in the screening station and passes through the porous passage for sensing by the dog.

22 Claims, 3 Drawing Sheets

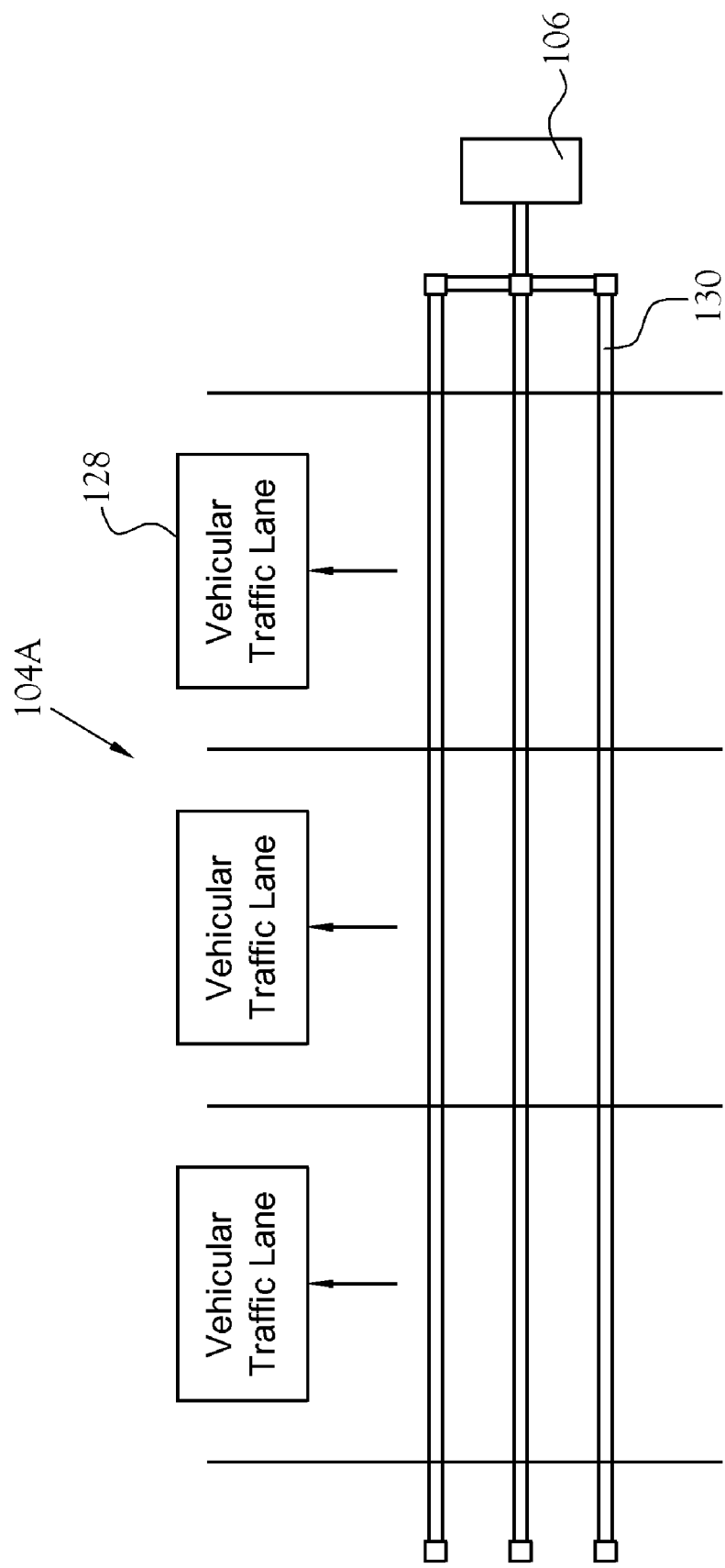

ODOR SCREENING SYSTEM

CROSS-REFERENCE TO RELATED APPLICATIONS

Not Applicable

STATEMENT REGARDING FEDERALLY-SPONSORED RESEARCH OR DEVELOPMENT

Not Applicable

BACKGROUND OF THE INVENTION

1. Field of Invention

The invention relates to a method and apparatus for screening pedestrians and vehicles for distinctive odors emitted by prohibited materials. More particularly the invention relates to a method and apparatus for collecting odor samples from pedestrians and vehicles and supplying the odor samples to a dog for identification of target odors of prohibited materials.

2. Description of the Related Art

There are many situations in which pedestrians or vehicles may be carrying materials which are prohibited from transport into or out of a designated area. Some examples are airports, sporting arenas and high security facilities. The prohibited materials may include, for example, explosives, drugs or even a product being stolen. Valuable products may be treated with a particular odor in order to easier to identify the products.

One method for screening for the materials is to individually search each pedestrian or vehicle for the prohibited material. Unfortunately, individual searching is extremely time-consuming and requires an inordinate number of searchers or an inordinate period of time.

It is known that many prohibited materials, such as explosives and drugs emit odors which are distinctive and can be detected in very small quantities by dogs which have been trained to identify such target odors. However, bringing a dog into direct contact with a large number of pedestrians or vehicles presents difficulties as well. Some people are fearful of dogs and others may cause harm to a highly trained dog or its handler. Traveling among a large number of vehicles may also create the potential for injury to a dog and/or its handler.

Accordingly, it is an object of the present invention to provide a method and apparatus for screening a plurality of pedestrians and/or vehicles for a prohibited material by collecting air samples from adjacent to the pedestrians or vehicles and transporting the samples to an enclosure containing a dog trained to identify the odor emitted by the prohibited material.

BRIEF SUMMARY OF THE INVENTION

In accordance with the present invention, pedestrians and/or vehicles are directed through a screening station. While they are located within the screening station, airflow is generated using ambient environment air. The airflow is directed through the screening station and over a pedestrian or vehicle to entrain odors emitted by the pedestrian or vehicle. The airflow carrying the entrained odors is directed to an enclosure containing a dog trained to identify one or more specific odors. The trained dog signals to a trainer when it has detected one of the odors for which it was trained, thus allowing the identification of carriers of prohibited materials while they are in the screening station.

BRIEF DESCRIPTION OF THE DRAWINGS

The above-mentioned features of the invention will become more clearly understood from the following detailed description of the invention read together with the drawings in which:

FIG. 3 is a plan view of the apparatus of FIG. 2.

DETAILED DESCRIPTION OF THE INVENTION

Figure 1:
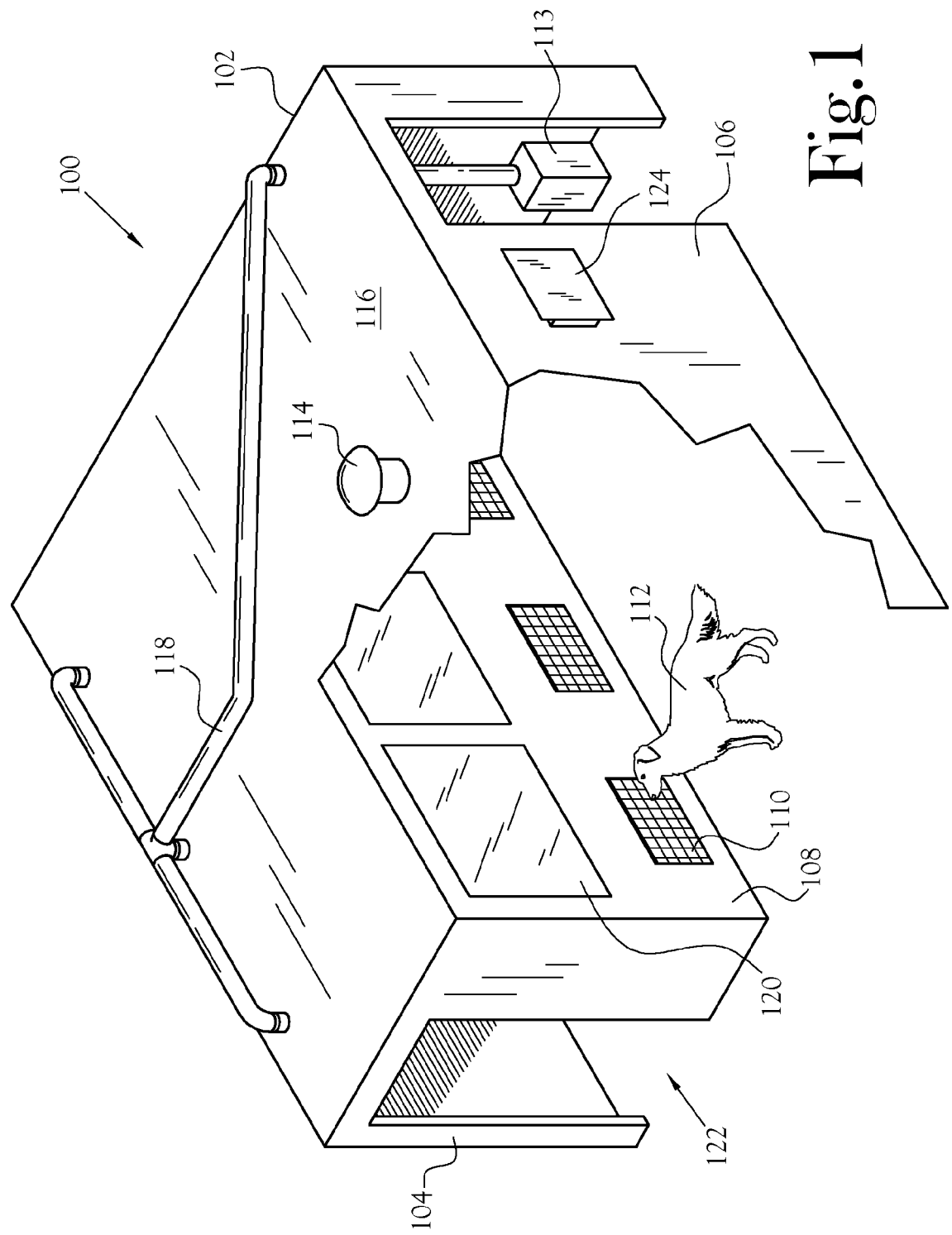
FIG. 1 is a partially cutaway perspective view of an apparatus for screening pedestrians in accordance with the present invention.

Referring to the drawings, in which similarly numbered objects represent similar objects, FIG. 1 illustrates an odor screening apparatus 100 according to the present invention.

The odor screening apparatus 100 comprises a structure 102 including a screening station 104 and an observation room 106. In the depicted embodiment, the wall 108 separates the screening station 104 from the observation room 106. The wall 108 includes an air permeable screen 110 which is located at a height adapted to the height of the particular type of a dog 112 being used in the system. The screen 110 provides a porous passage from the screening station to the observation room. In one embodiment the screen 110 is located about 18 inches above floor level. The screen 110 preferably allows the dog 112 to view pedestrians passing by through the screening station 104 as well as to collect airflow passing from the screening station 104 into the observation room 106.

An air conditioner 113 located in the observation room 106 is connected to the conduit 118. The conduit 118 leads out of the observation room 106 to the screening station 104 where it is dispersed through diffusers into the screening station 104. The air flow return of the air conditioning unit pulls the air from the diffusers in the screening station 104, through the screen(s) 110, into the observation room 106, and back into the return of the air conditioning unit 113. Ambient air is supplied to the system as pedestrians enter into the screening station. When cooler air supplies from the air conditioning unit 113 is not needed, the unit acts as a fan and continues to circulate air without cooling the air. Supplemental heaters may be used in the observation room 106 to supply heat for the comfort level of the dog and handler. In addition, a humidifier may be used in the observation room 106 to keep the humidity at an optimum level for canine detection of target odors. The sensitivity of the membranes of a canine's olfactory system can be affected by extremely low humidity levels.

A fan 114 is mounted upon the roof 116 of the structure 102 in the observation room 106 to draw additional ambient air from the environment if needed. An exhaust fan 124 is installed in the observation room 116. The fan 114 will remain off unless it should become necessary to evacuate the air from the observation room 106 and/or the screening station 104 due to any distracting odors that may enter the system. The screening process will cease until such distracting odors are evacuated and the fan 114 and exhaust fan 124 are turned off.

The entrance 122 and opposing exit (not shown) of the screening station 104 are designed to help control airflow into and out of the screening station 104 and ultimately into the observation room 106. This control may be accomplished by the use of different types of doors (revolving, sliding, folding,) or other barriers. When pedestrians enter the screening station 104, it is desirable to collect the air around them which could contain possible target odors. Therefore a weighted damper is used in the circulation system. This will cause an increase in the amount of air being pulled through the system when a person opens the door to enter the screening station 104. This increase in the cubic feet per minute of airflow at the entrance will result in the plume of air surrounding that person being pulled into the screening station 104 as the person enters. Additionally, once the person is in the screening station 104, they will be washed with air from the diffusers in the screening station 104. This air wash will cause the release of possible target odors from people's bodies, clothing, carried items or concealed objects they may be have in their possession. The plume of air and the washed air, along with possible target odors, will be pulled through the screen 110, into the observation room 106, where the air is presented to the dog 112 for analysis.

The screening station 104 is adapted to permit a limited number of pedestrians to pass through it at any given time. Preferably, the screening station 104 limits pedestrians to single file. However, a larger scale version would allow larger numbers of pedestrians to pass through it at any given time.

The wall 108 may include one or more panels 120, which may comprise either a window or a one-way glass. If the pedestrian cannot see into the observation room 106, he may assume that there is a dog within the room. Accordingly, there is a preventive effect even when there is no dog screening odors. Also, the pedestrian will not be aware that a screening dog has identified a target odor and will therefore be more easily apprehended. Using one-way glass, the visibility of the observation room can be controlled by contrasting the light levels within the observation room 106 and the screening station 104.

In operation, a dog 112 trained to identify at least one specific target odor is located in the observation room 106 where it can observe pedestrians walking through the screening station 104. The air conditioner 113 provides a continuous flow of air though the screening station 104 and through the screen 110 to the dog 112 in the observation room 106. As pedestrians are allowed to pass into and through the screening station 104, the airflow passing through the screening station 104 entrains odors emitted by the pedestrians and any packages or baggage they may be carrying. The entrained odors are then carried through the screen 110 for sensing by the dog 112. If the dog 112 senses the presence of target odor for which it has been trained, it will respond with a trained signal to alert a handler that a specific odor has been identified. The dog is rewarded and the handler, or other security officers, may then direct the interception of the pedestrian or group of pedestrians who emitted the detected odor. There should be enough distance between the canine detection center and the area being protected to allow for apprehension of suspect pedestrian traffic before the suspect(s) enter the area being protected from the introduction of the contraband substance. This distance will vary with other security factors particular to each application.

Figure 2:
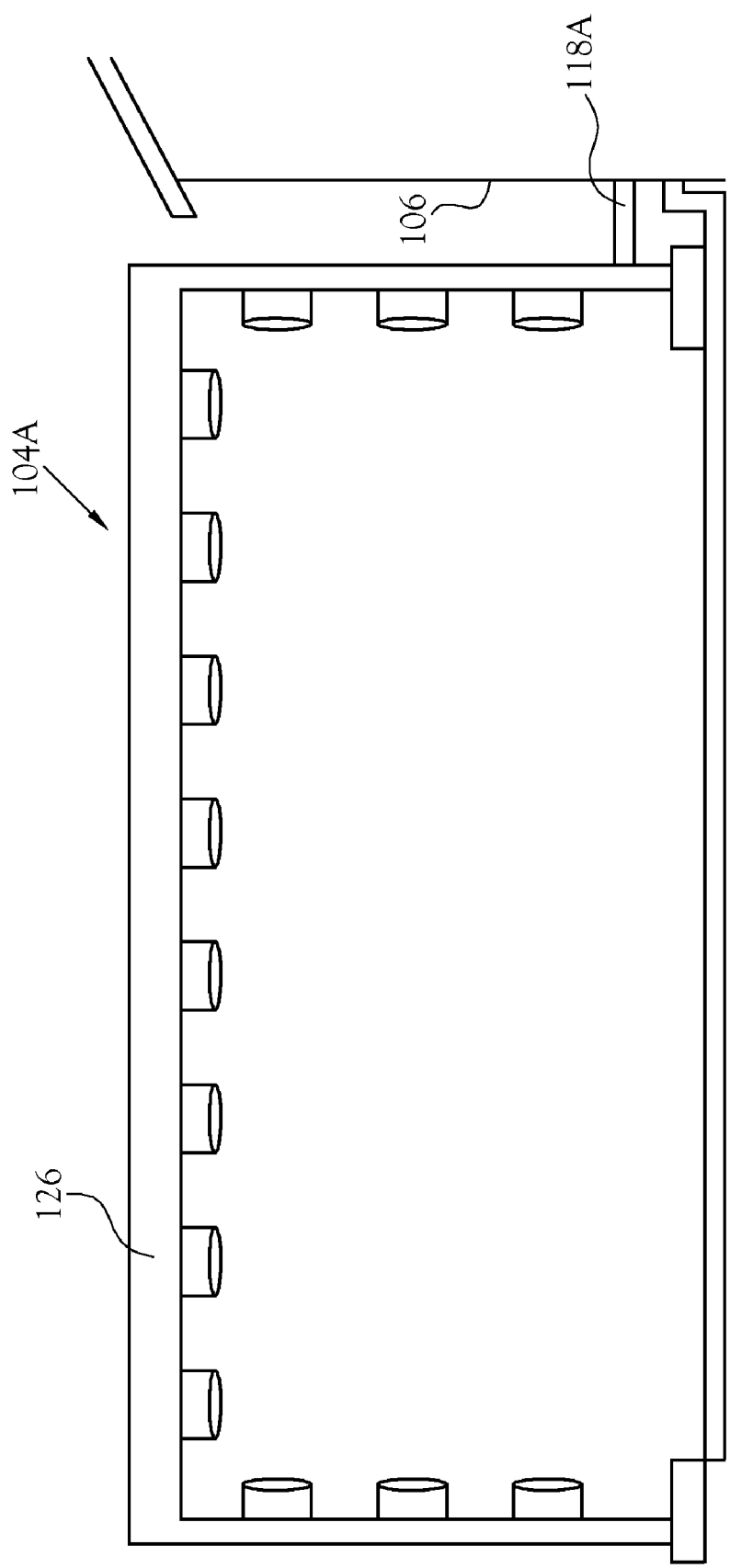
FIG. 2 is an elevation view of an apparatus for screening vehicles in accordance with the present invention.

As depicted in FIGS. 2 and 3, an alternative embodiment of a screening station 104A may be provided for screening odors emitted by vehicles. In this embodiment, a conduit 118A extends from the observation room 106 to a duct system 126 which extends upwardly an over one or more traffic lanes 128. A porous return duct 130 extends over the traffic lane(s) to collect air samples and carry them back into the observation room 106. In operation, ambient air is directed through the conduit 118A to the duct system 126 which directs airflow around vehicles as they pass through the duct system 126. Odors emitted by the vehicles or their contents is entrained in the airflow, which is captured by the porous return duct 130 and directed to the observation room 106 and the dog 112 contained therein. If the dog 112 senses the presence of the level of odor for which it has been trained, it will respond with a trained signal to alert a handler that a specific odor has been identified. The dog 112 is rewarded and the handler may then direct the detention of the vehicle which emitted the detected odor.

As desired, the pedestrians and vehicle drivers may or may not be informed of the presence of a trained dog 112 in the observation room 106. Providing the information may act as a deterrent.

A trained canine team can operate in the disclosed system with an efficiency rating of over 99%. The system of the present invention is particularly effective for identifying persons concealing explosives on their bodies or in packages or baggage. It allows for generally continuous movement of people while efficiently screening them for target odors While the present invention has been illustrated by description of several embodiments and while the illustrative embodiments have been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, what is claimed is:

1. An apparatus comprising:
    a screening station adapted to permit an odor emitter to pass through said screening station;
    an observation room;
    a dog located in the observation room and trained to identify at least one target odor;
    an airflow inducer for inducing airflow through the screening station to the observation room; and
    a porous passage from said screening station to said observation room, whereby air flows through said screening station, through said porous passage, and to the observation room to entrain odors in the observation room that were emitted in said screening station for sensing by said dog.

2. The apparatus of claim 1 wherein said porous passage comprises a screen in a wall separating said screening station from said observation room.

3. The apparatus of claim 1 wherein said porous passage comprises a porous return duct extending from said screening station to said observation room.

4. The apparatus of claim 1 wherein said airflow inducer comprises a fan and a conduit providing flow communication between said fan and said screening station.

5. The apparatus of claim 1 wherein the inducer for directing airflow through said screening station further comprises a plurality of diffusers for creating an air wash to release potential target odors from an odor emitter's body.

6. The apparatus of claim 1 wherein target odors are identified accurately with more than 99 percent accuracy.

7. The apparatus of claim 1 further comprising a weighted damper for capturing the air around an odor emitter as the odor emitter enters the screening station.

8. The apparatus of claim 1 wherein the observation room further comprises a temperature control apparatus.

9. The apparatus of claim 1 wherein the observation room further comprises a humidifier.

10. The apparatus of claim 1 comprising an entrance door and an exit door whereby an odor emitter enters the screening station through the entrance door and exits the screening station through the exit door.

11. The apparatus of claim 1 wherein a window is located in a wall separating said screening station from said observation room.

12. The apparatus of claim 11 and further comprising an exhaust fan in flow communication with said observation room.

13. The apparatus of claim 11 and further comprising a duct system adapted to extend over at least one vehicle lane.

14. A method of identifying the source of a target odor comprising the steps of:
   passing an odor emitter through the screening station of claim 1;
   directing airflow around said odor emitter to entrain odors;
   directing said airflow to an observation room containing a dog trained to detect a target odor.

15. The method of claim 14 and further comprising the step of allowing the odor emitter to observe the interior of the observation room.

16. The method of claim 14 and further comprising the step of preventing the odor emitter to observe the interior of the observation room.

17. The method of claim 14 and further comprising the step of allowing said dog to observe odor emitters passing though said screening station.

18. The method of claim 14 wherein the passing step further comprises passing a plurality of odor emitters in a single file fashion through the screening station.

19. The method of claim 14 wherein the passing step further comprises passing an odor emitter through the screening station wherein the odor emitter continuously moves through the screening station without completely stopping.

20. The method of claim 14 further comprising the step of:
   evacuating air from the observation room after a target odor or a distracting odor has been entrained in the observation room.

21. An apparatus comprising:
   a screening station adapted to permit an odor emitter to pass through said screening station;
   an observation room;
   a dog located in the observation room and trained to identify at least one target odor;
   a window located in a wall separating said screening station from said observation room;
   an airflow inducer comprising a fan and a conduit for inducing airflow through the screening station to the observation; and
   a porous passage from said screening station to said observation room comprising a screen in a wall separating said screening station from said observation room, whereby air flows through said screening station, through said porous passage, and to the observation room to entrain odors in the observation room that were emitted in said screening station for sensing by said dog.

22. The apparatus of claim 21 comprising an entrance door and an exit door whereby an odor emitter enters the screening station through the entrance door and exits the screening station through the exit door.

* * * * *